United States Patent [19]

Hiramoto et al.

[11] Patent Number: 5,285,166
[45] Date of Patent: Feb. 8, 1994

[54] METHOD OF EXTRACTING CHARGED PARTICLES FROM ACCELERATOR, AND ACCELERATOR CAPABLE OF CARRYING OUT THE METHOD, BY SHIFTING PARTICLE ORBIT

[75] Inventors: Kazuo Hiramoto, Hitachiota; Masatsugu Nishi, Katsuta; Akifumi Itano, Tokyo, all of Japan

[73] Assignees: Hitachi, Ltd., Tokyo; Director General of National Institute of Radiological Sciences, Chiba, both of Japan

[21] Appl. No.: 857,660

[22] Filed: Mar. 26, 1992

[30] Foreign Application Priority Data

Oct. 16, 1991 [JP] Japan .................... 3-267351

[51] Int. Cl.$^5$ ...................... H05H 7/00; H05H 11/00
[52] U.S. Cl. ...................... 328/233; 328/237
[58] Field of Search ............. 328/235, 233, 237

[56] References Cited

U.S. PATENT DOCUMENTS 3,328,708 6/1967 Smith et al. .................. 328/235
4,870,287 9/1989 Cole et al. ................... 328/235 X

OTHER PUBLICATIONS

"Medical Synchrotron for Proton Therapy" by Endo et al, Epac, Rome, Jun. 7–11, 1988, vol. 2, pp. 1459–1461. AIP Conference Proceedings 184, New York, 1989, pp. 80–91.

Primary Examiner—Donald J. Yusko
Assistant Examiner—John Giust
Attorney, Agent, or Firm—Antonelli, Terry, Stout & Kraus

[57] ABSTRACT

A method of extracting a strong, charged particle beam, that is, a large current from an accelerator, and an accelerator capable of carrying out the method utilizes charged particles which are extracted from the accelerator. The equilibrium orbit of charged particles in one of a bending magnet and a magnet having multipole components greater than sextuple components, is shifted by a constituent element of the accelerator other than these magnets, to change the tune of charged particles. The adjustment of this tune based upon the shift of the equilibrium orbit in the above magnet for extracting charged particles, can keep the gradient of orbit of the extracted beam substantially constant. Accordingly, beam extraction is readily controlled, and a large current can be extracted from the accelerator.

30 Claims, 10 Drawing Sheets

FIG.1
PRIOR ART

FIG.2B PRIOR ART
FINAL STAGE OF BEAM EXTRACTION

FIG.2A PRIOR ART
INITIAL STAGE OF BEAM EXTRACTION

METHOD OF EXTRACTING CHARGED PARTICLES FROM ACCELERATOR, AND ACCELERATOR CAPABLE OF CARRYING OUT THE METHOD, BY SHIFTING PARTICLE ORBIT

BACKGROUND OF THE INVENTION

The present invention relates to a method of extracting a charged particle beam from an accelerator, and an accelerator capable of carrying out the method.

In a conventional circular accelerator, accelerated electrons or ions are extracted from the accelerator, to be used for physical experiments, medical purposes, or others. Further, as discussed on pages 53 to 61 of the AIP Conference Proceedings No. 127 (1983), the third order resonance or half integer resonance of betatron oscillation is used for extracting the accelerated electrons or ions from the accelerator.

Figure 1:
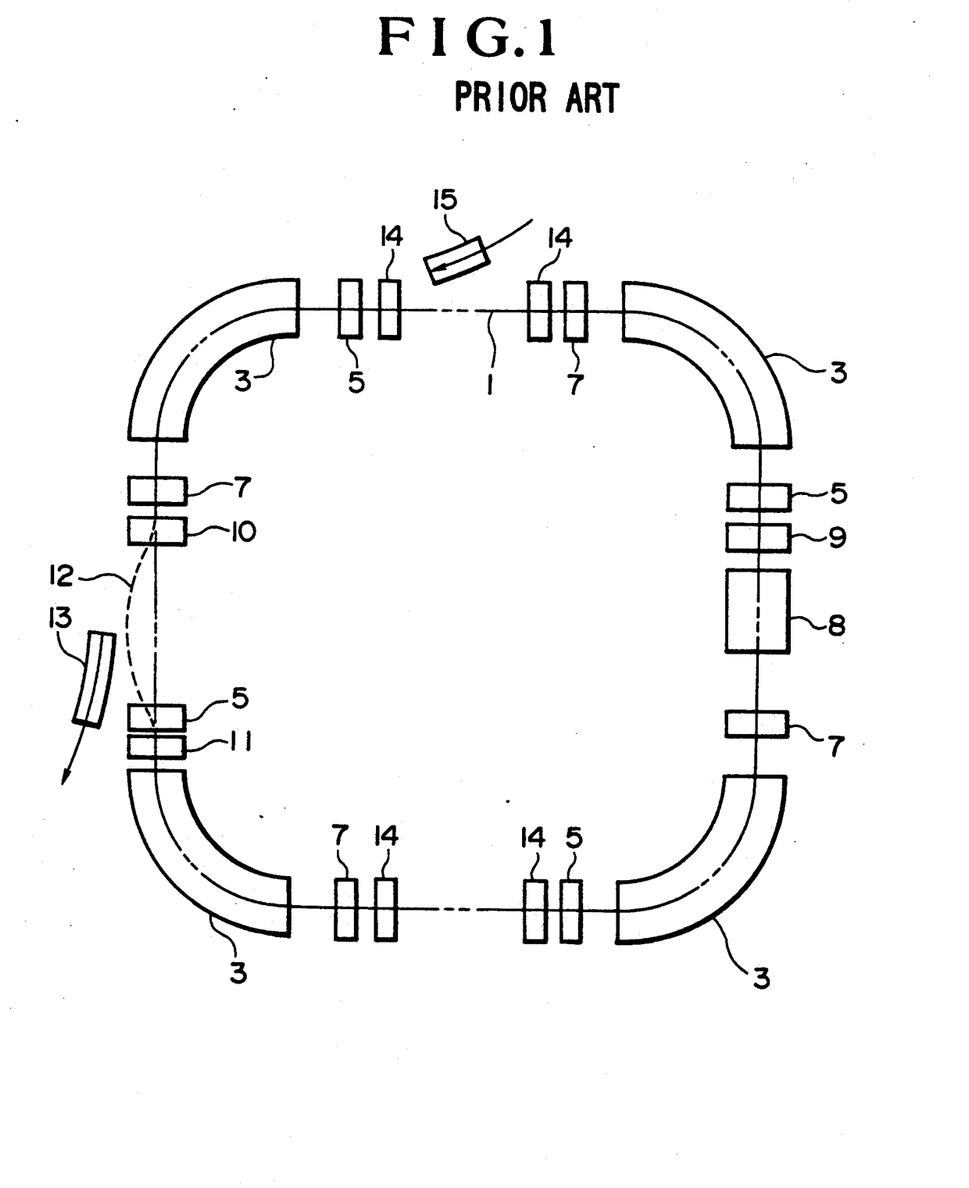
FIG. 1 is a schematic diagram showing a conventional circular accelerator.

FIG. 1 shows an example of the conventional accelerator. Referring to FIG. 1, charged particles injected from an inflector 15 circulate stably around an equilibrium orbit 1 (that is, closed loop, around which charged particles can revolve stably) while making betatron oscillations, with the aid of bending magnets 3, focusing quadrupole magnets 5 and defocusing quadrupole magnets 7. Further, the charged particles acquire energy when they pass through an accelerating cavity 8. In such an accelerating process, the tune of charged particles, that is, the number of betatron oscillations per one revolution of a charged particle along the equilibrium orbit, is usually set, in both of horizontal and vertical directions, to an integer $\pm \frac{1}{4}$, with the aid of the focusing magnets 5 and the defocusing magnets 7.

The betatron oscillation of third order resonance or the half integer resonance are excited, when the accelerated, charged particle beam is extracted from the accelerator. In order to extract the beam from the accelerator in the horizontal or vertical direction, the tune in the horizontal or vertical direction is adjusted in the following manner with the aid of the quadrupole magnets 5 and 7. That is, in the case of the half integer resonance, the tune is made to approach an integer $\pm \frac{1}{4}$. While, in a case where the third order resonance is used, the tune is made to approach an integer $\pm \frac{1}{3}$. In this state, the half integer resonance is generated by exciting an octupole magnet which is previously installed in the accelerator, or the third order resonance is generated by exciting a (for example, sextupole magnet 5 of FIG. 1). Thus, the betatron oscillation of the half integer resonance or the third order resonance are excited, and the amplitude of betatron oscillations of charged particles over a stable limit increases to a great degree. Further, in order to prevent the charged particle beam in this state from colliding with a duct, a pair of dipole, bump magnets 10 and 11 are excited to shift that portion of the equilibrium orbit which exists in the neighborhood of a deflector 13 for extraction, to the deflector side, thereby forming a bumped orbit 12 (that is, a locally distorted orbit).

Figure 2A:
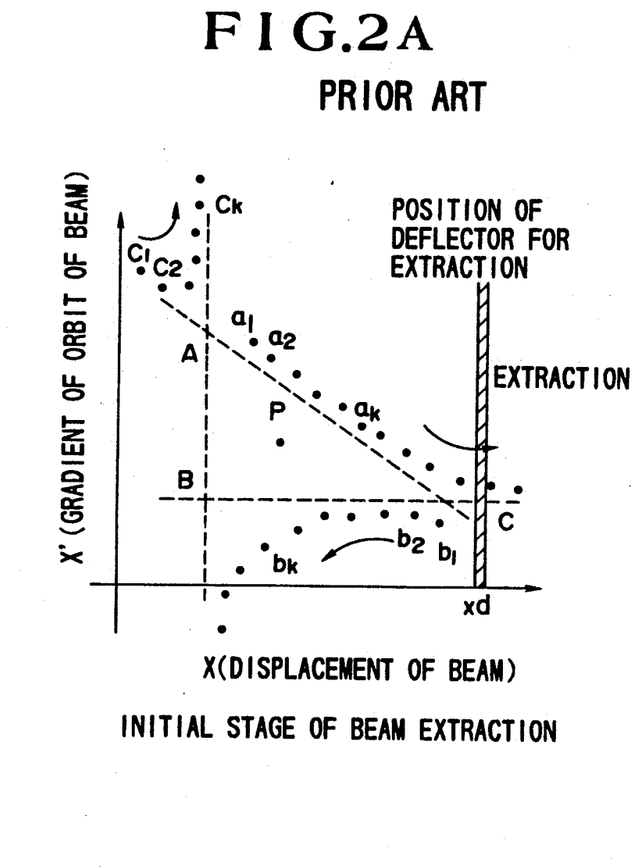
FIGS. 2A and 2B are figures showing phase spaces in the initial and last stages of extraction of charged particles from the accelerator of FIG. 1.
Figure 2B:
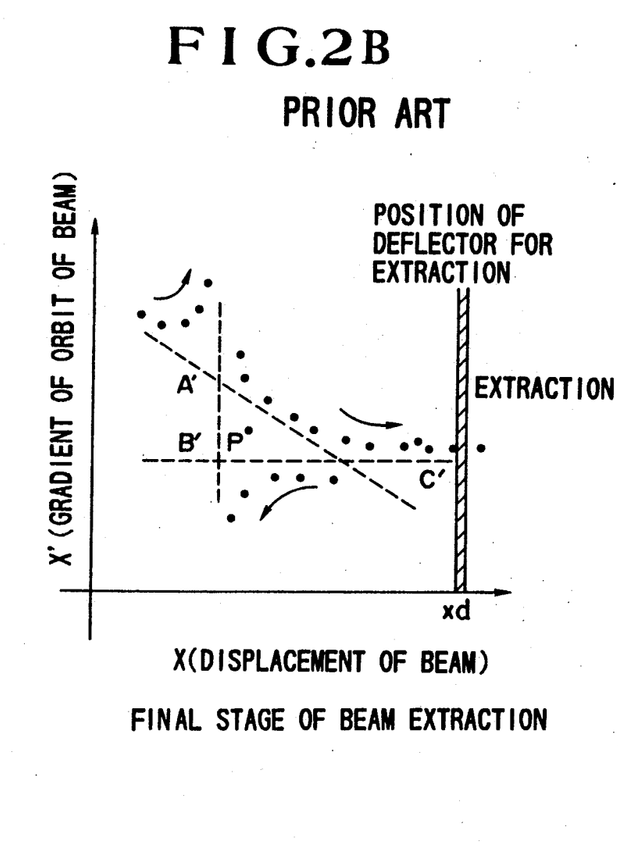

The behavior of the beam at this time will be explained below, with reference to phase spaces shown in FIGS. 2A and 2B. FIGS. 2A and 2B show phase spaces in the initial and last stages of beam extraction at the deflector due to the third order resonance, respectively. In FIGS. 2A and 2B, the abscissa indicates the displacement x of the beam in the horizontal direction, and the ordinate indicates the gradient of orbit x' of the beam (where $x' = dx/ds$, and s indicates a distance in the circular orbit direction). In the case where the third order resonance is used, a triangular separatrix (that is, stable limit) such as the triangle $\Delta ABC$ of FIG. 2A is formed. Further, in this case, the tune is nearly equal to an integer $\pm \frac{1}{3}$. Accordingly, a charged particle is put in substantially the same state position with the phase space, after three revolutions along the equilibrium orbit. That is, each charged particle can be put in three states at an extraction point. In FIGS. 2A and 2B, three directed curves indicate the transition of three states of each charged particle, on the outside of the separatrix. For example, a charged particle in the state $a_1$ of FIG. 2A is put in a state $b_1$ after having made one revolution along the equilibrium orbit, is put in a state $c_1$ after having made two revolutions, and is put in a state $a_2$ after having made three revolutions. Finally, the charged particle reaches the deflector 13 which is spaced apart from the equilibrium orbit a distance $x_d$, and thus is extracted from the accelerator A portion of charged particles revolving along the equilibrium orbit is large in amplitude of betatron oscillation, and another portion of the charged particles is small in the above amplitude. In order to extract charged particles gradually from the accelerator, the charged particles are extracted in order of amplitude of betatron oscillations. Accordingly, the separatrix is made relatively large in the initial stage of extraction as shown in FIG. 2A, and is made small with time. This operation is performed by a supplementary quadrupole magnet 14 shown in FIG. 1, or by a supplementary coil mounted on each of a pair of quadrupole magnets 5 and 7. That is, the tune approaches an integer $\pm \frac{1}{3}$ with the aid of the supplementary quadrupole magnet 14 or the supplementary coil mounted on each of a pair of quadrupole magnets 5 and 7, and thus the separatrix is reduced to the triangle $\Delta A'B'C'$ of FIG. 2B.

As can be seen from the trajectory of each charged particle shown in FIGS. 2A and 2B, when the charged particle beam is extracted from the accelerator in the above-mentioned manner, the gradient of orbit of the extracted beam in the initial stage of extraction having a large separatrix such as the triangle $\Delta ABC$ of FIG. 2A is different from the gradient of orbit of the extracted beam in the last stage of extraction having a small separatrix such as the triangle $\Delta A'B'C'$ of FIG. 2B, and thus there arises a problem that it is impossible to extract a strong, charged particle beam.

Recently, it is required to make the accelerator small in size and to use the accelerator for industrial or medical purpose. However, when the fine adjustment of the tune for extracting charge particles is made by the supplementary quadrupole magnet 14 in a small-sized accelerator, interference will be generated between the supplementary quadrupole magnet 14 and other constituent elements of the accelerator. Thus, an accelerator can not be made small in size.

SUMMARY OF THE INVENTION

It is a first object of the present invention to provide an accelerator, from which a strong, charged particle beam, that is, a large current can be extracted.

It is a second object of the present invention to provide a small-sized accelerator which can dispense with a supplementary quadrupole magnet or a pair of quadrupole magnets each provided with a supplementary coil.

It is a third object of the present invention to provide a method of and an apparatus for extracting a charged particle beam which produces a large current, from an accelerator.

In order to attain the first and third objects, according to the present invention, the tune of charged particles is changed by shifting the equilibrium orbit of charged particles in one of a bending magnet and a magnet having multipole components greater than six poles.

Further, in order to attain the second object, according to the present invention, the equilibrium orbit of charged particles in one of the above magnets is shifted by a constituent element of the accelerator other than these magnets.

In the conventional accelerator, the tune of charged particles is changed by the supplementary quadrupole magnet or a pair of quadrupole magnets each provided with the supplementary coil. While, in an accelerator according to the present invention, the tune is changed by shifting the equilibrium orbit of charged particles in one of the bending magnets and the magnets having multipole components greater than six poles.

Further, according to the present invention, a bumped orbit is formed at an extraction point, and a change in gradient of orbit of the charged particle beam at the extraction point due to the above change in tune is cancelled by a change in the gradient of the bumped orbit. Thus, the change in gradient of orbit of the beam at the extraction point is reduced.

The equilibrium orbit of charged particles in one of the bending magnets and the magnet having multipole components greater than six poles, can be shifted by an element which is included in the accelerator and used for a specified purpose, for example, a bump magnet for generating the bumped orbit or a high-frequency accelerating cavity for accelerating charged particles. Accordingly, the accelerator can dispense with the supplementary quadrupole magnet 14, and thus can be made small in size.

Next, explanation will be made of the reason why the tune can be adjusted by controlling the equilibrium orbit.

Figure 3:
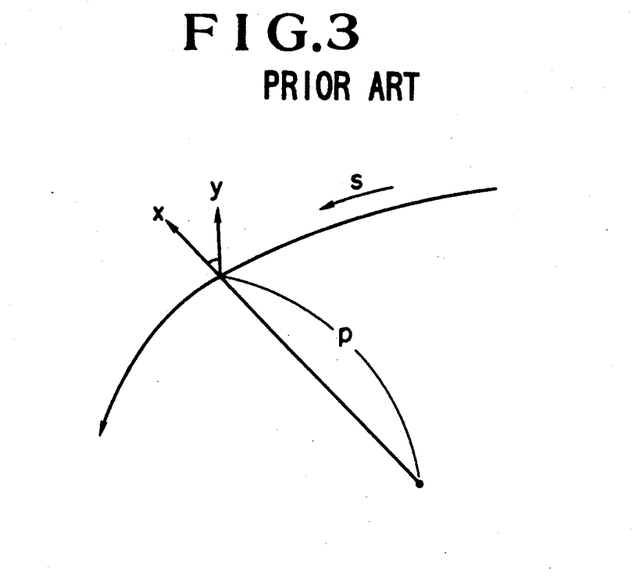
FIG. 3 shows a coordinate system which is used for explaining the basic principle of the present invention.

First, let us consider a case where the equilibrium orbit in the bending magnet is shifted to adjust the tune. The coordinate system in the heading magnet is shown in FIG. 3. When the displacement of the charged particle beam and the gradient of orbit thereof are expressed by x and x', respectively, the betatron oscillations in the bending magnet are expressed by the following equations:

$$\frac{dx}{ds} = x' + \frac{x}{\rho} x' \qquad (1)$$

$$\frac{dx'}{ds} = -\frac{x}{\rho^2} - \frac{x^2}{2\rho} \qquad (2)$$

As can be seen from the equations (1) and (2), in a case where both of the displacement x and the gradient x' of orbit are small or the radius $\rho$ of curvature is large, the second term on the right-hand side of each of the equations (1) and (2) can be neglected. Thus, the displacement x is given by the following, linear-oscillation indicating equation:

$$\frac{d^2x}{ds^2} = -\frac{x}{\rho^2} \qquad (3)$$

Accordingly, the tune does not depend upon the magnitude of each of the variables x and x'. While, in a case where both of the variables x and x' are large, or the radius $\rho$ of curvature is small, the second term on the right-hand side of each of the equations (1) and (2) cannot be neglected. Thus, the displacement x is given by the following, nonlinear-oscillation indicating equation:

$$x'' = -\frac{x}{\rho^2} - \frac{x^2}{\rho^3} + \frac{x'^2}{2\rho} + \frac{xx'^2}{2\rho^2} \qquad (4)$$

In this case, owing to the second to fourth terms on the right-hand side of the equation (4), the tune varies depending upon the magnitude of each of the displacement x and the gradient x'. This phenomenon does not occur in the conventional accelerator having a large radius of curvature. In the present invention, the above phenomenon is utilized to change the tune and to control the size of the separatrix.

Next, in order to show that the tune varies in accordance with the shift of the equilibrium orbit in a magnet having multipole components greater than six poles, the orbit in a sextupole magnet will be explained, by way of example. The displacement x of the equilibrium orbit in the sextupole magnet is given by the following equation:

$$\frac{dx^2}{ds^2} = -S_x x^2 \qquad (5)$$

where $S_x$ is a coefficient dependent upon the magnetic field intensity of the sextuple magnet. In a case where the coefficient $S_x$ is positive, the tune increases or decreases according as the displacement x is positive or negative. While, in a case where the coefficient $S_x$ is negative, the tune decreases or increases according as the displacement x is positive or negative.

As mentioned above, the tune can be changed by shifting the equilibrium orbit of charged particles in a bending magnet or resonance exciter magnet which is a sextupole magnet. The size of a separatrix for charged particles to be extracted can be controlled by the above shift of equilibrium orbit. Additionally, the gradient of orbit of the extracted, charged particle beam can be controlled by adjusting a bumped equilibrium orbit at an extraction point.

DESCRIPTION OF THE PREFERRED EMBODIMENTS

Figure 4:
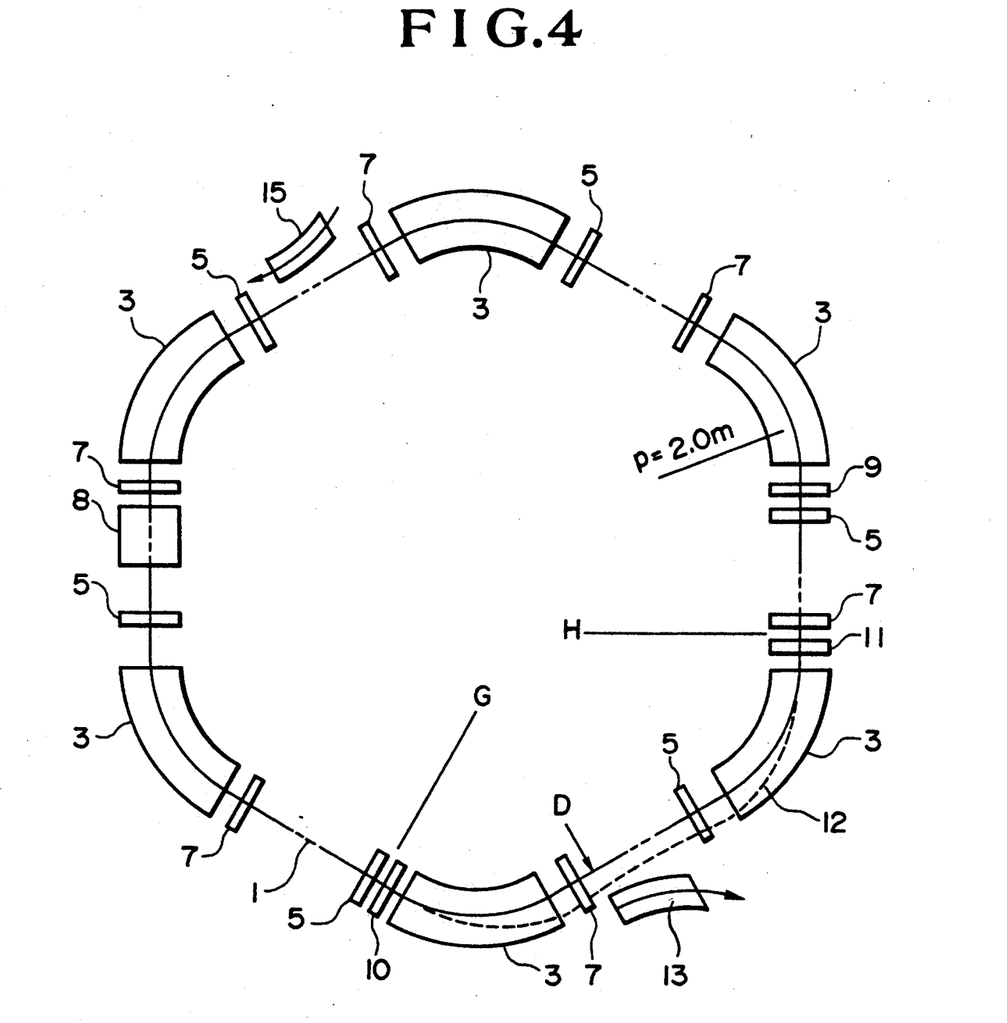
FIG. 4 is a schematic diagram showing an embodiment of an accelerator according to the present invention.

FIG. 4 shows an embodiment of an accelerator according to the present invention which embodiment is a circular accelerator for medical use. Referring to FIG. 4, the whole circumference of the embodiment is made up of six superperiods corresponding to a regular hexagon, and has a length of 37 m. In an accelerator for extracting charged particles, therefrom, as shown in FIG. 4, each pair of quadrupole magnets 5 and 7 are geometrically symmetric with respect to a midpoint. A proton beam having an energy of 10 MeV is injected from an inflector 15 for injection, into the present embodiment, and thus a beam having an emittance of 40 $\pi$mm.mrad revolves in the embodiment, with the aid of a bending magnet 3 having a curvature radius of 2.0 m and a length of 2.1 m, a defocusing quadrupole magnet 7 having a length of 0.2 m, and a focusing quadrupole magnet 5 having a length of 0.2 m. In more detail, the beam revolves along an equilibrium orbit 1 while making betatron oscillation and being accelerated by a high-frequency accelerating cavity 8. At this time, the magnetic field intensity of each of the bending magnet 3, the focusing quadrupole magnet 5 and the defocusing quadrupole magnet 7 is increased in proportion to an increase in momentum of the beam due to the acceleration thereof. In this accelerating process, the quadrupole magnets 5 and 7 are excited so that the tune in the horizontal direction is 1.75 and the tune in the vertical direction is 1.25.

When the beam is accelerated to a maximum energy of 100 MeV in the above-mentioned manner, the beam has an emittance of 12 $\pi$mm.mrad. Then, the supply of high frequency energy from the cavity 8 to the beam is stopped while keeping the magnetic flux density of the bending magnet 3 at 0.7 T. As a result, the beam which has revolved in bunches for a period when high frequency energy is supplied to the beam, revolves along the equilibrium orbit as a continuous beam. Further, in this state, the focusing quadrupole magnet 5 and the defocusing quadrupole magnet 7 are excited so that the tune in the horizontal direction is 1.75 and the tune in the vertical direction is 1.25.

The beam is extracted from the present embodiment by a deflector 13 for extraction. Accordingly, bump magnets 10 and 11 are installed on the upstream and downstream sides of the deflector 13, respectively. As shown in FIG. 4, when the bump magnets 10 and 11 are excited, a bumped orbit 12 passes through the bending magnet 3, and the tune is changed for the following reason.

Figure 5:
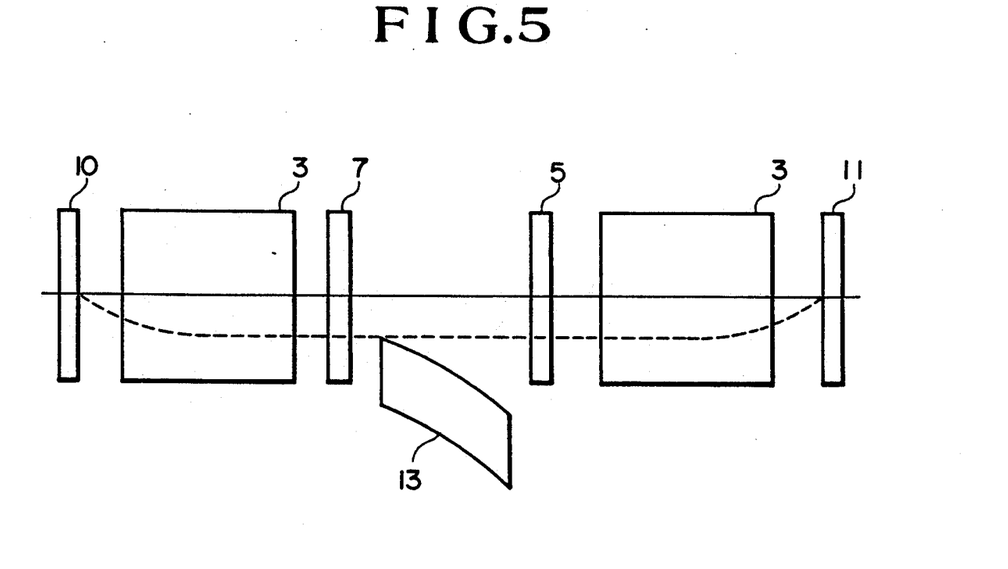
FIG. 5 is a diagram showing a part of the embodiment of FIG. 4.

FIG. 5 shows that part of the embodiment of FIG. 4 which is bounded by two lines G and H. In the present embodiment, the equilibrium orbit 1 of the beam is distorted so that the bumped orbit 12 passes through the bending magnet 3 (or a sextupole magnet 9). Incidentally, the sextupole magnet 9 is used for correcting a change in the tune due to the deviation of momentum of the beam from a design value, that is, for correcting chromaticity. Such a quadrupole magnet is included in some of conventional accelerators. The bumped orbit 12 can be formed by bump dipole magnets 10 and 11. When the bumped orbit 12 is formed so as to pass through the bending magnet 3 (or sextupole magnet 9), the tune is changed according to the reason having been already mentioned. Prior to the extraction of the beam, the bump magnets 10 and 11 are excited so that the magnet 10 has a magnetic flux density of 0.3 T and the magnet 11 has a magnetic flux density of 0.36 T, to form the bumped orbit. Simultaneously with the formation of the bumped orbit, the focusing quadrupole magnet 5 and the defocusing quadrupole magnet 7 are adjusted so that the magnet 5 has a magnetic field gradient of 0.60 T/m and the magnet 7 has a magnetic field gradient of 2.09 T/m. By making the above adjustment, the tune in the horizontal direction becomes 1.67 nearly equal to a value for the third order resonance, while keeping the tune in the vertical direction at 1.25 (it is to be noted that when the magnetic flux density of each of the bump magnets 10 and 11 is reduced to one-third of the above-mentioned value, the tune in the horizontal direction becomes equal to 5/3).

Figure 6:
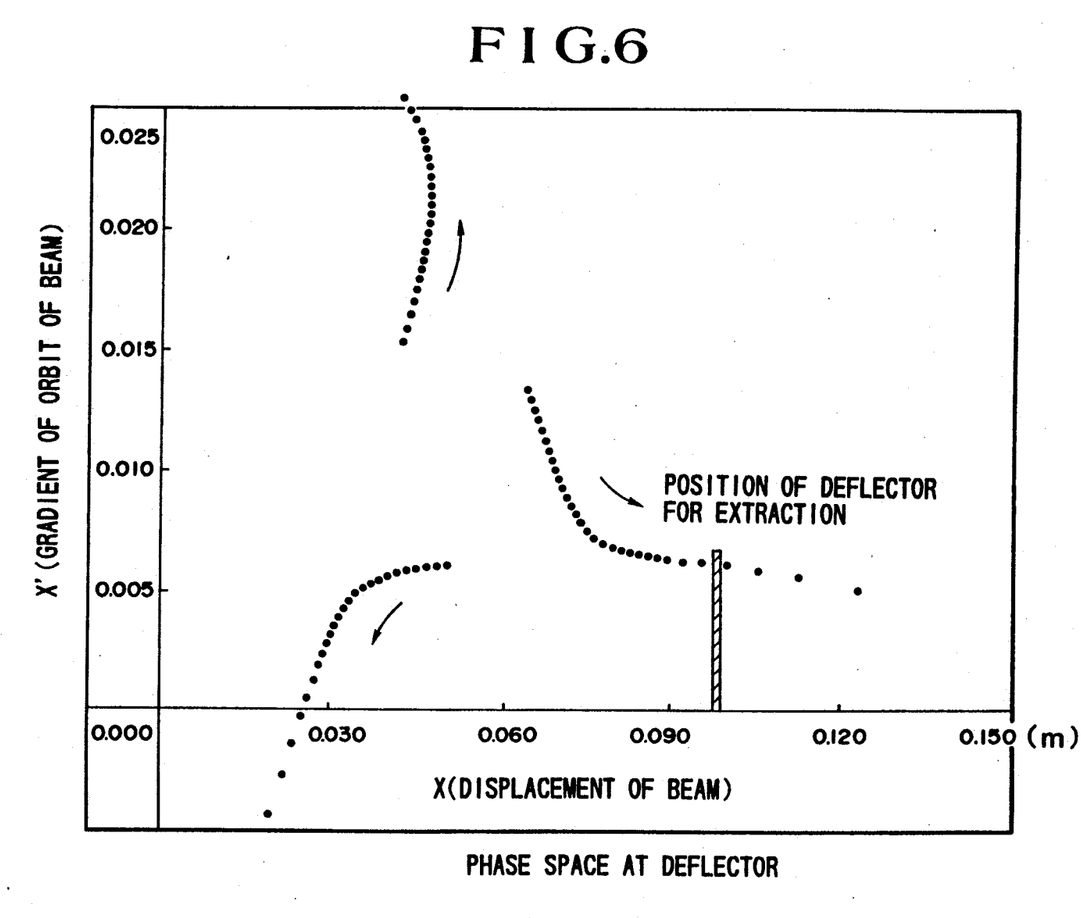
FIGS. 6 and 7 are figures showing phase spaces in the initial and last stages of extraction of charged particles from the embodiment of FIG. 4.

In this stage, a resonance exciting sextrupole magnet 9 having a length of 0.2 m is excited so as to have a magnetic field intensity of 18 T/m$^2$. Then, owing to the third order resonance, the amplitude of the beam having a maximum amplitude and an emittance of 10 $\pi$mm.mrad, becomes large gradually. FIG. 6 shows the trajectory of each proton in a phase space at a position D where the deflector 13 for extraction is disposed. The deflector 13 is spaced apart from the equilibrium orbit a distance 100 mm in the horizontal direction. As can be seen from FIG. 6, each proton enters the deflector 13 along an orbit having a gradient of 6 mrad, after 150 revolutions, to be extracted from the accelerator.

Figure 7:
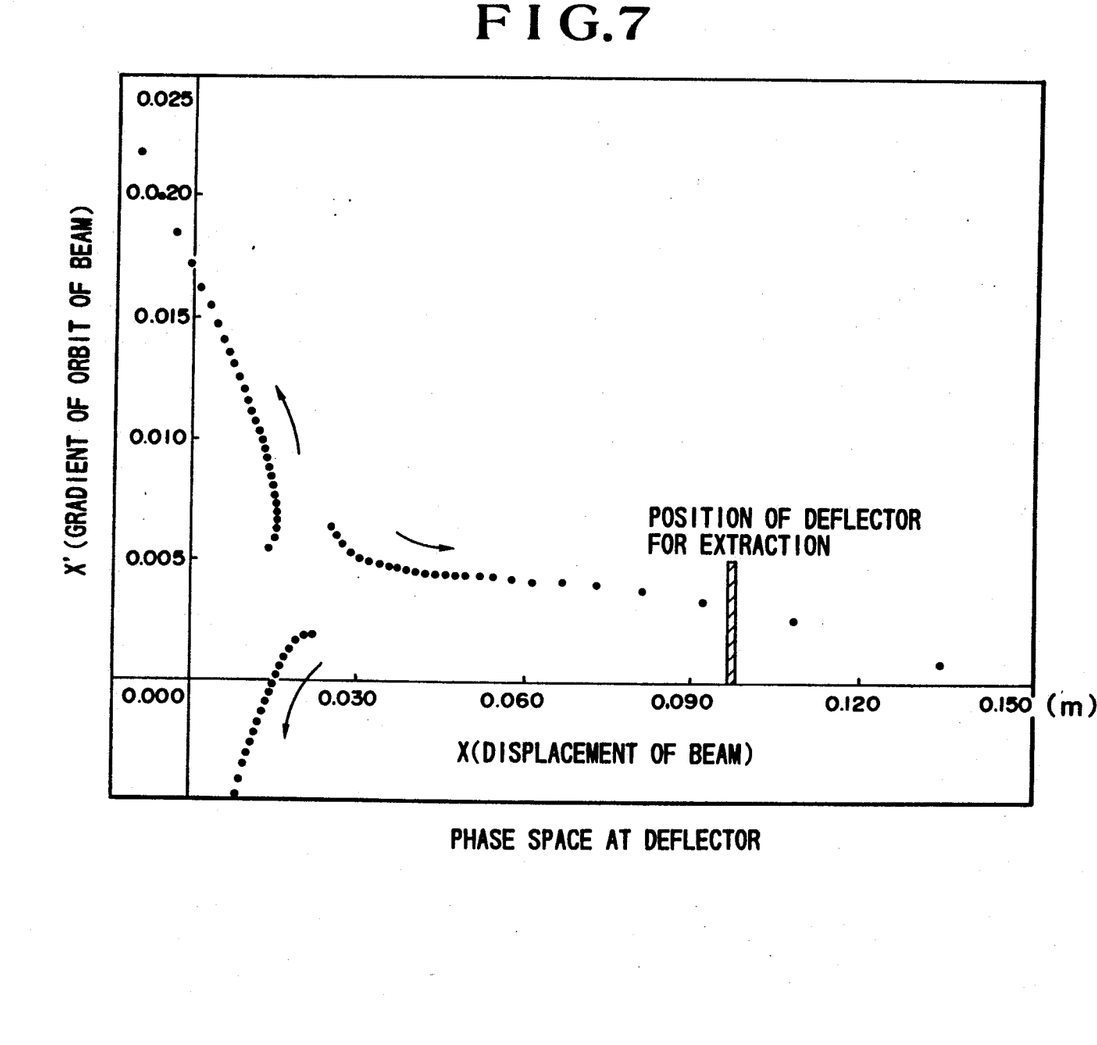

Next, exciting currents for the bump magnets 10 and 11 are reduced for a period of 0.1 sec so that the magnet 10 has a magnetic flux density of 0.1 T and the magnet 11 has a magnetic flux density of 0.12 T. Thus, the tune in the horizontal direction gradually changes from 1.67 to 5/3. As a result, the stable limit becomes small gradually. Thus, as shown in FIG. 7, a proton which is small in amplitude of betatron oscillation, can be extracted from the accelerator along an orbit having a gradient of about 4 mrad.

Further, a phenomenon that the gradient of bumped orbit at the center of a stable limit is reduced in the above extraction process, will suppress an increase in the gradient of orbit of extracted beam caused by reducing the stable limit (which increase is apparent from FIGS. 2A and 2B). Thus, as can be seen from the comparison between FIGS. 6 and 7, a difference in the gradient of orbit of the extracted beam between the initial and final stages of beam extraction, is reduced to about 2 mrad, without adjusting the deflection angle of the deflector.

As has been explained in the above, according to the present embodiment, the fine adjustment of the tune which has hitherto been made by the supplementary quadrupole magnet 14 of FIG. 1, can be made by changing the exciting currents for the bump magnets 10 and 11. Thus, the present embodiment can dispense with the supplementary quadrupole magnet 14. That is, according to the present embodiment, by changing the exciting currents for the bump magnets, the tune is varied, the separatrix is made small, and protons small in amplitude of betatron oscillations can be extracted. Further, by changing the above exciting currents, the gradient of bumped orbit at the extraction position, that is, the gradient of orbit at the extraction position for the separatrix formed in a phase space is varied.

In more detail according to the present embodiment, by shifting the equilibrium orbit in the bending magnet 5 or the sextupole magnet, not only the tune is changed and the separatrix in a phase space is made small, but also the gradient of the bumped orbit changes so that the change in the gradient of the bumped orbit is opposite in direction to a change in the gradient of orbit of the extracted beam in a period from the initial stage of beam extraction to the final stage thereof (In FIGS. 2A and 2B, the gradient of orbit of the extracted beam changes in a positive direction, that is, increases in the above period). Thus, the change in the gradient of orbit of the extracted beam is suppressed. In other words, the fine adjustment of the tune and the adjustment of the gradient of orbit of the extracted beam which are both made by the supplementary quadrupole magnet 14 in the conventional accelerator of FIG. 1, are made by changing the exciting currents for the bump magnets 10 and 11.

As mentioned above, according to the present embodiment, the magnetic flux density of each of the bump magnets 10 and 11 for forming the bumpled orbit is changed to shift the equilibrium orbit (bumped orbit) in the bending magnet (or sextupole magnet), thereby changing the tune. Further, by adjusting the gradient of the bumped orbit, a change in the gradient of orbit of the extracted beam is reduced to 2 mrad. Additionally, a small-sized accelerator can be constructed which can dispense with the supplementary quadrupole magnet for adjusting the tune.

Figure 8:
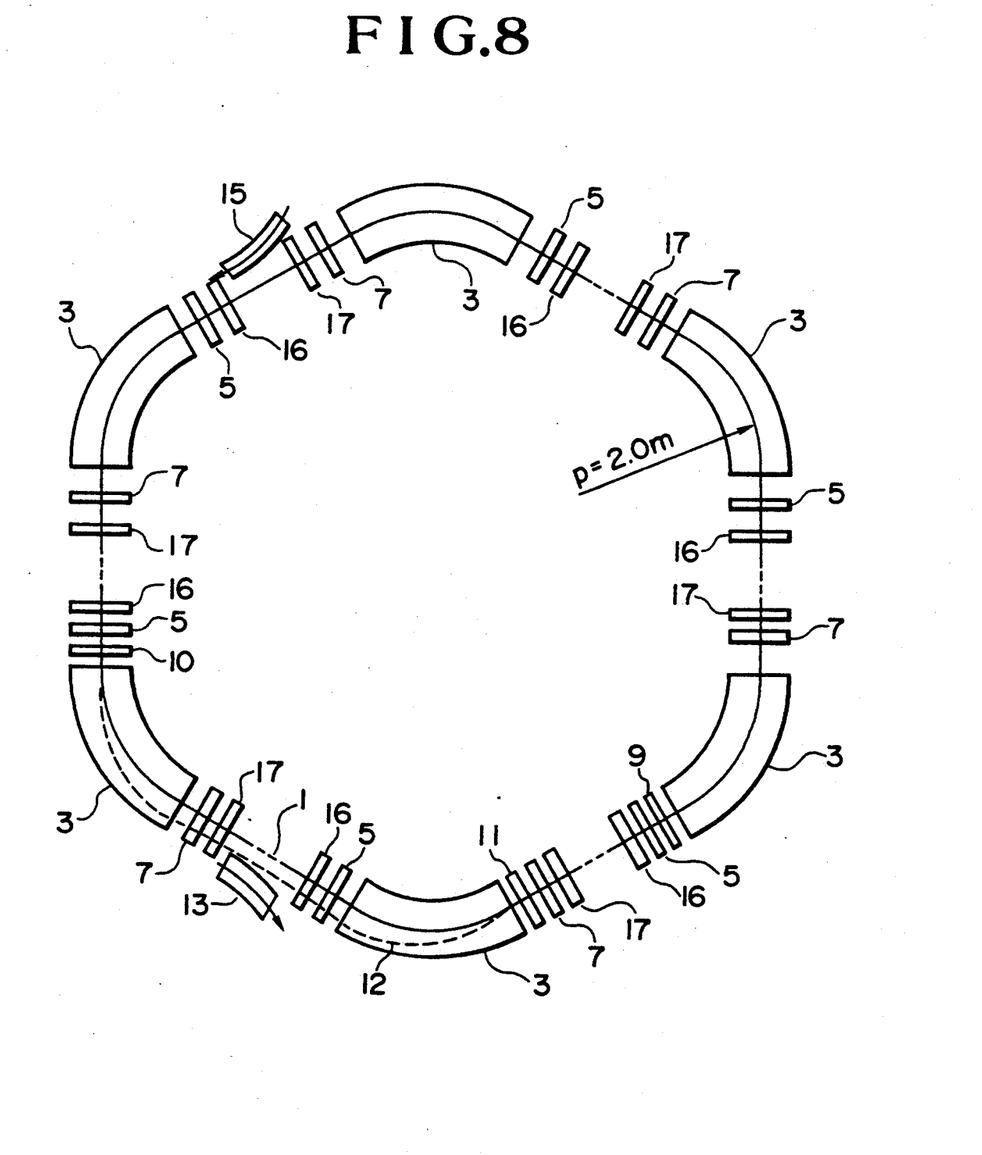
FIG. 8 is a schematic diagram showing another embodiment of an accelerator according to the present invention.
Figure 9A:
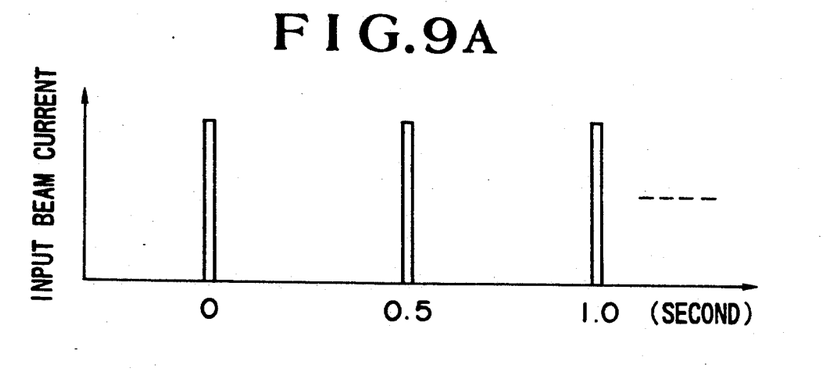
FIGS. 9A, 9B and 9C are graphs showing the variation of an input beam current, the magnetic field intensity of bump magnet and an extracted current, with time.

FIG. 8 shows another embodiment of an accelerator according to the present invention, in which embodiment a pulsive ion beam is stored, to be converted into a continuous ion beam. The whole circumference of the present embodiment has a length of 37 m, and is made up of six superperiods. Referring to FIG. 8, a pulsive proton beam having an energy of 50 MeV is injected from the inflector 15 for injection, into the present embodiment. The pulsive proton beam has an emittance of 10 $\pi$mm.mrad and a duration time of 100 $\mu$s, and is injected from a linac (not shown) twice a second, as shown in FIG. 9A. Further, the injected beam has a momentum spread of $\pm 0.1\%$, and beams having various momentum values are continuously extracted from a storage ring (that is, present embodiment).

The beam injected from the inflector 15 revolves stably in the storage ring, with aid of the bending magnet 3 having a radius of curvature of 2.0 m, the focusing quadrupole magnet 5 and the defocusing quadrupole magnet 7. In this state, the magnetic field gradient of the magnet 5 and that of the magnet 7 are set to 0.42 T/m and 1.46 T/m, respectively, to make the tune in the horizontal direction and the tune in the vertical direction equal to 1.67 and 1.25, respectively. Further, the magnetic flux density of the bending magnet 3 is set to 0.6 T so that the beam has a radius of curvature of 2 m. As mentioned above, the injected beam has a momentum spread of $\pm 1\%$. In order to correct a change in the tune due to variations in momentum, a focusing sextupole magnet 16 and a defocusing sextupole magnet 17 are installed in each of linear portions of the storage ring, as shown in FIG. 8. The magnetic field intensity of the magnet 16 and that of the magnet 17 are set to 2.8 T/m$^2$ and 3.6 T/m$^2$, respectively.

Figure 9B:
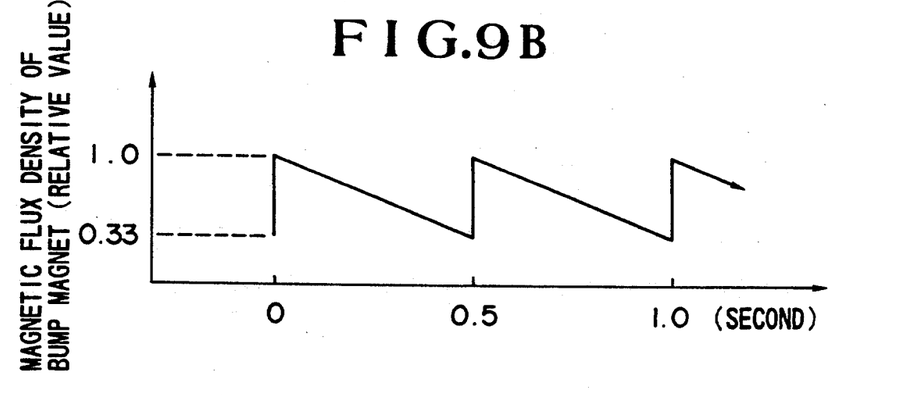
Figure 9C:
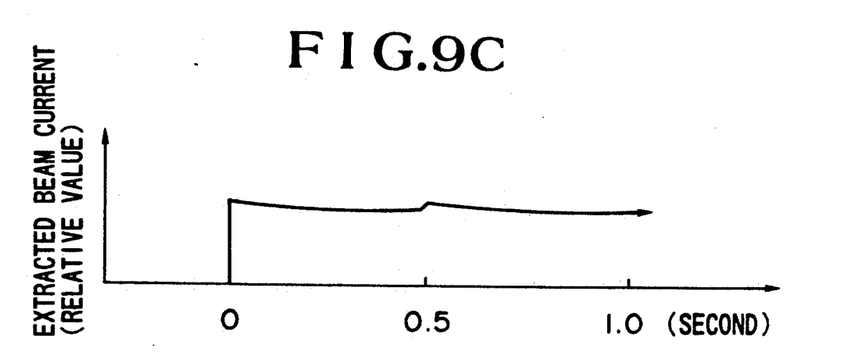
Figure 10:
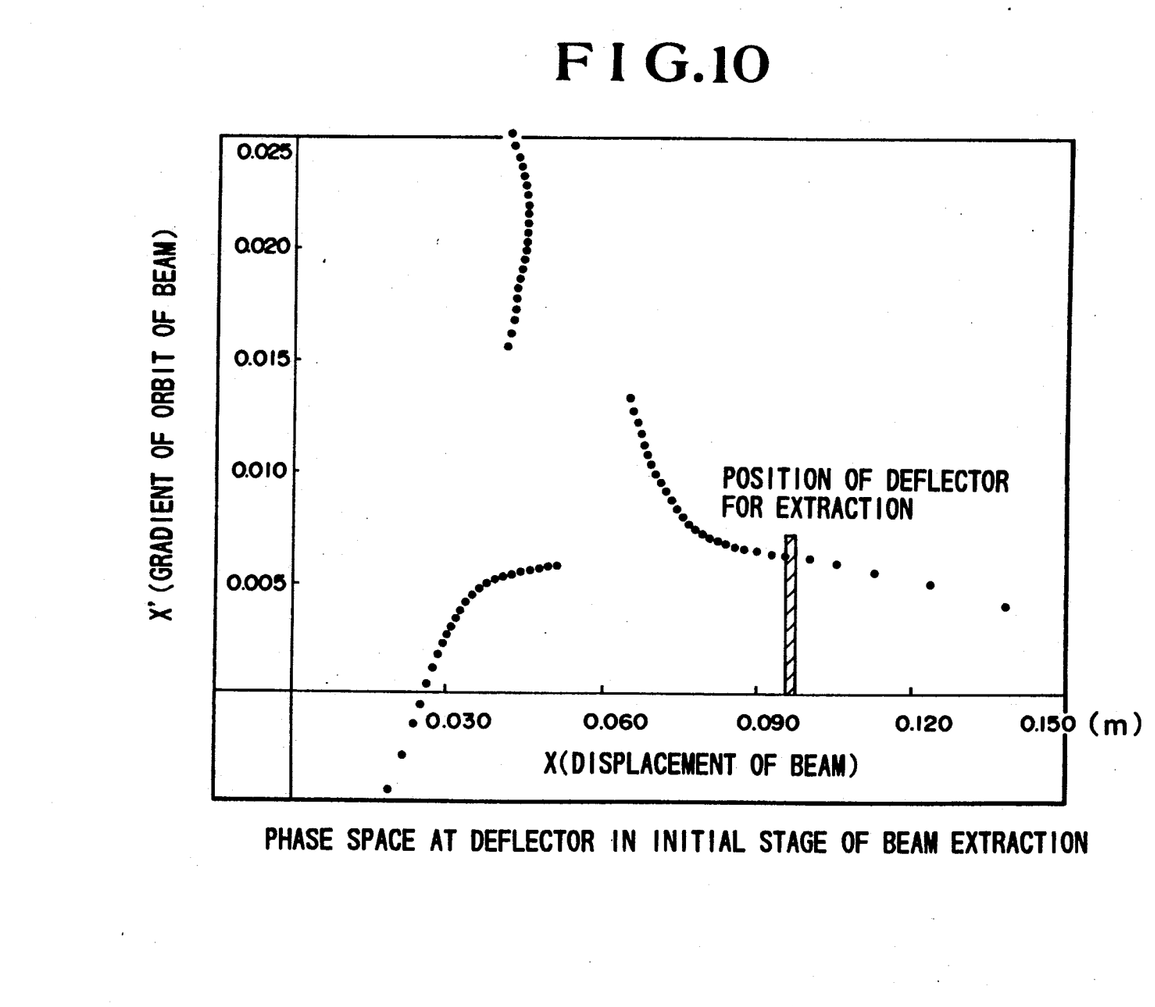
FIGS. 10 and 11 are graphs showing phase spaces in the initial and final stages of extraction of charged particles from the embodiment of FIG. 8.
Figure 11:
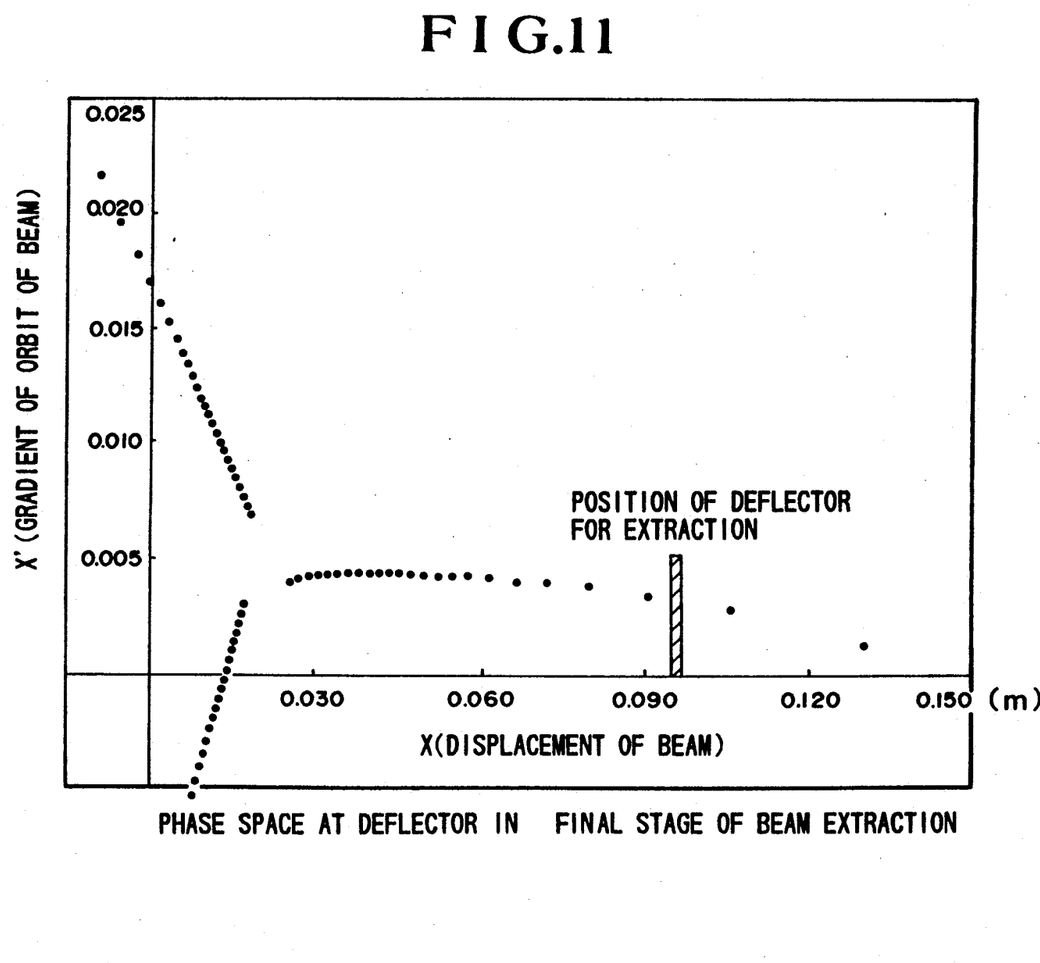

Prior to the extraction of the beam, the bump magnets 10 and 11 are excited to have a magnetic flux density of 0.2 T and a magnetic flux density of 0.24 T, respectively. Thus, the bumped orbit 12 passes through a pair of bending magnets 3 and the sextupole magnets 16 and 17. Further, the resonance-exciting sextupole magnet 9 is previously excited so as to have a magnetic field intensity of 12 T/m$^2$. In this stage, the tune is different from a value for the resonance by about 0.001, and thus the beam revolves stably. Next, the magnetic flux density of the bump magnet 10 is reduced from 0.2 T to 0.07 T and the magnetic flux density of the bump magnet 11 is reduced from 0.24 T to 0.08 T, at intervals of 0.5 sec as shown in FIG. 9B. Hence, the tune in the horizontal direction is reduced to 1.666 . . . in a period of 0.5 sec as shown in FIG. 9C. As a result, as can be seen from those phase spaces at the deflector 13 which are shown in FIGS. 10 and 11, protons are extracted from the storage ring in order of amplitude of betatron oscillations, and moreover the gradient of orbit of the extracted beam is kept substantially constant.

In the above embodiments, the equilibrium orbit of charged particles in a bending magnet or magnet having multipole components greater than six poles, is shifted by adjusting the bumped orbit. Alternatively, the above equilibrium orbit may be shifted by a different method. For example, the equilibrium orbit may be shifted by adjusting a relation among accelerating frequencies used in the high-frequency accelerating cavity, or a cavity only for shifting the above equilibrium orbit may be installed on the circular orbit of an accelerator.

As has been explained previously, according to the present invention, the tune is adjusted by shifting the equilibrium orbit in a bending magnet or magnet having multipole components greater than six poles. Further, when the tune is changed in the above manner, the gradient of orbit of the extracted beam is kept substantially constant. Thus, the extraction of beam is readily controlled, and an accelerator capable of extracting a large current therefrom can be obtained. Furthermore, a small-sized accelerator can be obtained which can dispense with a supplementary quadrupole magnet for adjusting the tune.

We claim:

1. A method of extracting a charged particle beam from an accelerator by exciting a betatron oscillation of charged particles to a specified resonance, comprising a step of changing a resonant state of the betatron oscillation by shifting an equilibrium orbit of the charged particles in one of a bending magnet and a magnet having multipole components greater than six poles, the magnets being included in the accelerator.

2. A method according to claim 1, wherein said accelerator is circular and includes:
   a plurality of bending magnets;
   a plurality of bumping magnets;
   a plurality of quadrupole magnets;
   a plurality of magnets having multipole components higher than a sextupole component;
   a radio frequency accelerating cavity; and
   a deflector for the extraction by exciting the specified resonance to the betatron oscillations.

3. A method of extracting a charged particle beam from an accelerator by exciting an betatron oscillation of charged particles to a specified resonance comprising a step of changing a size of a region indicative of a stable limit at a time when the betatron oscillation is excited to the specified resonance, by shifting an equilibrium orbit of charged particles in one of a bending magnet and a magnet having multipole components greater than six poles, the magnets being included in the accelerator.

4. A method according to claim 3, wherein said accelerator is circular and includes:
   a plurality of bending magnets;
   a plurality of bumping magnets;
   a plurality of quadrupole magnets;
   a plurality of magnets having multipole components higher than a sextupole component;
   a radio frequency accelerating cavity; and
   a deflector for the extraction by exciting the specified resonance to the betatron oscillations.

5. A method of extracting a charged particle beam from an accelerator in such a manner that a betatron oscillation of charged particles is excited to a specified resonance and a region indicative of a stable limit at a time when the betatron oscillation is excited to the specified resonance, is gradually reduced in a period from an initial stage of the extraction of the charged particle beam to a last stage of the extraction of the charged particle beam, the method comprising a step of shifting an equilibrium orbit of charged particles in one of a bending magnet and a magnet having multipole components greater than six poles, to change a tune of the charged particles, thereby decreasing a region indicative of the stable limit at a time when the betatron oscillation is excited to the specified resonance, gradually in the period from the initial stage of extraction of the charged particle beam to the last stage of the extraction of the charged particle beam.

6. A method according to claim 5, wherein the equilibrium orbit in one of the magnets is greatly shifted in the initial stage of the extraction of the charged particle beam and is slightly shifted in the last stage of the extraction of the charged particle beam, to make the tune gradually approach a value at the specified resonance.

7. A method according to claim 5, wherein a period when the charged particle beam is extracted from the accelerator, is controlled by changing a speed, at which the equilibrium orbit in one of the magnets is shifted.

8. A method according to claim 5, wherein said accelerator is circular and includes:
   a plurality of bending magnets;
   a plurality of bumping magnets;
   a plurality of quadrupole magnets;
   a plurality of magnets having multipole components higher than a sextupole component;
   a radio frequency accelerating cavity; and
   a deflector for the extraction by exciting the specified resonance to the betatron oscillations.

9. A method of extracting a charged particle beam from an accelerator in such a manner that a betatron oscillation of charged particles is excited to a specified resonance and a region indicative of a stable limit at a time when the betatron oscillation is excited to the specified resonance, is gradually reduced in a period from an initial stage of the extraction of the charged particle beam to a last stage of the extraction of the charged particle beam, the method comprising a step of maintaining a gradient of orbit of the extracted beam substantially constant.

10. A method according to claim 9, wherein an equilibrium orbit of charged particles is shifted so that the gradient of orbit of the extracted beam is kept substantially constant.

11. A method according to claim 9, wherein said accelerator is circular and includes:
   a plurality of bending magnets;
   a plurality of bumping magnets;
   a plurality of quadrupole magnets;
   a plurality of magnets having multipole components higher than a sextupole component;
   a radio frequency accelerating cavity; and
   a deflector for the extraction by exciting the specified resonance to the betatron oscillations.

12. A method of extracting a charged particle beam from an accelerator by exciting a betatron oscillation of charged particles to a specified resonance, comprising steps of:
   forming a bumped orbit of charged particles in one of a bending magnet and a magnet having multipole components greater than six poles, the magnets being included in the accelerator; and
   shifting the bumped orbit to change a resonant state of the betatron oscillation.

13. A method according to claim 12, wherein said accelerator is circular and includes:
   a plurality of bending magnets;
   a plurality of bumping magnets;
   a plurality of quadrupole magnets;
   a plurality of magnets having multipole components higher than a sextupole component;
   a radio frequency accelerating cavity; and
   a deflector for the extraction by exciting the specified resonance to the betatron oscillations.

14. An accelerator for extracting a charged particle beam therefrom by exciting a betatron oscillation of charged particles to a specified resonance, comprising:
   a bending magnet for making charged particles travel along a circular orbit;
   an extraction point where the charged particles are extracted from the circular orbit;
   a resonance exciter magnet for exciting the betatron oscillation to the specified resonance; and
   means for shifting the equilibrium orbit of charged particles in one of the bending magnet and a magnet having multiple components greater than six poles to change a tune of the charged particles.

15. An accelerator according to claim 14, further comprising:
   a plurality of bending magnets;
   a plurality of resonance exciter magnets; and
   a plurality of magnets having multipole components higher than a sextupole component.

16. An accelerator for extracting a charged particle beam therefrom by exciting a betatron oscillation of charged particles to a specified resonance, comprising:
   a bending magnet for making charged particles travel along a circular orbit;
   an extraction point where the charged particles are extracted from the circular orbit;
   a resonance exciter magnet for exciting the betatron oscillation to the specified resonance; and
   means for shifting the equilibrium orbit of charged particles in one of the bending magnet and a magnet having multiple components greater than six poles, to change a tune of the charged particles.

17. An accelerator according to claim 16, further comprising:
   a plurality of bending magnets;
   a plurality of resonance exciter magnets;
   a plurality of magnets having multipole components higher than a sextupole component; and
   a plurality of magnets for shifting the equilibrium orbit of the charged particles.

18. An accelerator for extracting a charged particle beam therefrom by exciting a betatron oscillation of charged particles to a specified resonance, comprising:
- a bending magnet for making charged particles travel along a circular orbit;
- a sextuple magnet for exciting the betatron oscillation to the specified resonance;
- an extraction point where the charged particles are extracted from the circular orbit; and
- a magnet for shifting an equilibrium orbit of charged particles in one of the bending magnet and a sextuple magnet other than the resonance-exciting sextuple magnet, to change the tune of the charged particles.

19. An accelerator according to claim 18, further comprising:
- a plurality of bending magnets;
- a plurality of resonance exciter magnets;
- a plurality of magnets having multipole components higher than a sextupole component; and
- a plurality of magnets for shifting the equilibrium orbit of the charged particles.

20. An accelerator for extracting a charged particle beam therefrom by exciting a betatron oscillation of charged particles to a specified resonance, comprising:
- a bending magnet for making charged particles travel along a circular orbit;
- an octupole magnet for exciting the betatron oscillation to the specified resonance; and
- an extraction point where the charged particles are extracted from the circular orbit;
- a magnet for shifting an equilibrium orbit of charged particles in one of the bending magnet and a magnet which has multipole components greater than six poles and is different from the octupole magnet, to change the tune of the charged particles.

21. An accelerator according to claim 20, further comprising:
- a plurality of bending magnets;
- a plurality of octupole magnets;
- a plurality of magnets which have multipole components higher than a sextupole component; and
- a plurality of magnets for shifting the equilibrium orbit.

22. An accelerator for extracting a charged particle beam therefrom by exciting a betatron oscillation of charged particles to a specified resonance, comprising:
- a multiplicity of bending magnets for making charged particles travel along a circular orbit;
- a multiplicity of focusing quadrupole magnets and defocusing quadrupole magnets for focusing and defocusing the charged particle beam, respectively, each of the quadrupole magnets being devoid of a supplementary coil for beam extraction; and
- means for extracting charged particles from the circular orbit.

23. An accelerator according to claim 22, wherein said means for extracting charged particles from the circular orbit, shifts and equilibrium orbit.

24. An accelerator for extracting a charged particle beam therefrom by exciting a betatron oscillation of charged particles to a specified resonance, comprising:
- a multiplicity of magnets for making charged particles travel along a circular orbit; and
- extraction means for extracting the charged particles from the circular orbit, the extraction means being provided with means for keeping a gradient of orbit of the extracted beam substantially constant.

25. An accelerator for extracting a charged particle beam therefrom by exciting a betatron oscillation of charged particles to a specified resonance, comprising:
- a bending magnet for making charged particles travel along a circular orbit;
- extraction means for extracting the charged particles from the circular orbit, the extraction means being provided with means for keeping a gradient of orbit of the extracted beam substantially constant;
- a resonance exciter magnet for exciting the betatron oscillation to the specified resonance; and
- means for shifting an equilibrium orbit of charged particles in one of the bending magnet and a magnet having multipole components greater than six poles, the change the tune of the charged particles.

26. An accelerator according to claim 25, further comprising:
- a plurality of bending magnets;
- a plurality of resonance exciter magnets; and
- a plurality of magnetic having multipole components higher than a sextupole component.

27. An accelerator for extracting a charged particle beam therefrom by exciting a betatron oscillation of charged particles to a specified resonance, comprising:
- an extractor for extracting charged particles;
- a bending magnet;
- a resonance exciter magnet for exciting the betatron oscillation to the specified resonance; and
- means for shifting an equilibrium orbit of charged particles in one of the bending magnet and the resonance exciter magnet.

28. An accelerator according to claim 27, further comprising:
- a plurality of bending magnets; and
- a plurality of resonance exciter magnets.

29. An apparatus for extracting a charged particle beam from an accelerator by exciting a betatron oscillation of charged particles to a specified resonance, comprising:
- an extractor including an extraction point for extracting the charged particles; and
- means for maintaining a gradient of orbit of the extracted beam at the extraction point substantially constant.

30. An apparatus according to claim 29, wherein said accelerator is circular and includes:
- a plurality of bending magnet;
- a plurality of bumping magnets;
- a plurality of quadrupole magnets;
- a plurality of magnets having multipole components higher than sextupole component;
- a radio frequency accelerating cavity; and
- a deflector for the extraction by exciting the specified resonance of the betatron oscillations.

* * * * *